(12) United States Patent
Moskovich

(10) Patent No.: US 8,042,214 B2
(45) Date of Patent: Oct. 25, 2011

(54) ORAL CARE IMPLEMENT

(75) Inventor: Robert Moskovich, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 125 days.

(21) Appl. No.: 12/560,894

(22) Filed: Sep. 16, 2009

(65) Prior Publication Data

US 2010/0004666 A1    Jan. 7, 2010

Related U.S. Application Data

(60) Division of application No. 11/261,048, filed on Oct. 28, 2005, now Pat. No. 7,594,293, which is a continuation-in-part of application No. 11/011,605, filed on Dec. 15, 2004, now Pat. No. 7,725,980, and a continuation-in-part of application No. 11/019,671, filed on Dec. 23, 2004, now Pat. No. 7,721,376, which is a continuation-in-part of application No. 10/869,922, filed on Jun. 18, 2004, now Pat. No. 7,143,462, which is a continuation-in-part of application No. 10/601,106, filed on Jun. 20, 2003, now abandoned, said application No. 11/019,671 is a continuation-in-part of application No. PCT/US03/30633, filed on Sep. 26, 2003, said application No. 11/019,671 is a continuation-in-part of application No. PCT/US03/29497, filed on Sep. 17, 2003, said application No. 11/019,671 is a continuation-in-part of application No. 29/189,729, filed on Sep. 10, 2003, now Pat. No. Des. 517,812, which is a continuation-in-part of application No. 10/989,267, filed on Nov. 17, 2004, now Pat. No. 7,607,189, which is a continuation-in-part of application No. 29/209,242, filed on Jul. 14, 2004, now abandoned.

(60) Provisional application No. 60/414,117, filed on Sep. 27, 2002, provisional application No. 60/418,776, filed on Oct. 16, 2002, provisional application No. 60/419,425, filed on Oct. 18, 2002, provisional application No. 60/412,290, filed on Sep. 20, 2002.

(51) Int. Cl.
*A61B 17/24* (2006.01)
*A61H 13/00* (2006.01)
*A46B 9/04* (2006.01)

(52) U.S. Cl. ............. 15/111; 15/110; 15/167.1; 15/187; 15/188; 601/141; 606/161

(58) Field of Classification Search ............ 15/105, 15/110, 111, 117, 167.1, 187, 188; 601/135, 601/137–139, 141; 606/161
See application file for complete search history.

(56) References Cited

U.S. PATENT DOCUMENTS 585,358 A    6/1897    Gould
(Continued)

FOREIGN PATENT DOCUMENTS

DE    857128    11/1952
(Continued)

*Primary Examiner* — Mark Spisich
(74) *Attorney, Agent, or Firm* — Judy W. Chung

(57) ABSTRACT

An oral care implement with a soft tissue cleanser is provided to effectively cleanse the soft tissue of the mouth with comfort and a reduced risk of injury to the user. In one construction, a projection is formed of a combination of a hard material and a soft material. The hard material provides good stability for cleaning debris from the tongue or other tissue while the soft material provides comfort and a reduced risk of injury.

10 Claims, 3 Drawing Sheets

U.S. PATENT DOCUMENTS

| | | | |
|---|---|---|---|
| 697,336 A | 4/1902 | Hagerty | |
| 726,727 A | 4/1903 | Mills | |
| 864,054 A | 8/1907 | Abrams | |
| 907,842 A | 12/1908 | Meuzies | |
| 1,002,468 A | 9/1911 | Strangman | |
| 1,006,630 A | 10/1911 | Clarke | |
| 1,125,532 A | 1/1915 | Himmel | |
| 1,128,139 A | 2/1915 | Hoffman | |
| 1,142,698 A | 6/1915 | Crumbaugh | |
| 1,153,409 A | 9/1915 | Wheeler | |
| 1,191,556 A * | 7/1916 | Blake | 15/117 |
| 1,251,250 A | 12/1917 | Libby | |
| 1,268,544 A | 6/1918 | Cates | |
| 1,470,710 A | 10/1923 | Davis | |
| 1,495,675 A | 5/1924 | Colt | |
| 1,598,224 A | 8/1926 | Van Sant | |
| 1,658,706 A | 2/1928 | Carrott | |
| D75,971 S | 8/1928 | Faubert et al. | |
| 1,704,564 A | 3/1929 | Friedland | |
| 1,705,109 A | 3/1929 | Essbach | |
| 1,726,560 A | 9/1929 | Hassler | |
| 1,728,956 A | 9/1929 | Darmitzel | |
| 1,741,143 A | 12/1929 | Chin | |
| 1,816,582 A | 7/1931 | Heron | |
| 1,817,585 A | 8/1931 | Samuel | |
| 1,860,924 A | 5/1932 | Cooke | |
| 1,861,347 A | 5/1932 | Johnson | |
| 1,872,832 A | 8/1932 | Silverberg | |
| 1,891,864 A * | 12/1932 | Barrett | 606/161 |
| 1,892,068 A | 12/1932 | Metzler | |
| 1,903,161 A | 3/1933 | Barkan | |
| 1,993,662 A | 3/1935 | Green | |
| 1,993,763 A | 3/1935 | Touchstone | |
| D99,352 S * | 4/1936 | Grapp | D4/136 |
| 2,042,239 A | 5/1936 | Planding | |
| 2,049,956 A | 8/1936 | Greenberg | |
| 2,059,914 A | 11/1936 | Rosenberg | |
| 2,079,728 A | 5/1937 | Arnold | |
| 2,083,217 A | 6/1937 | Brothers et al. | |
| 2,129,082 A | 9/1938 | Byrer | |
| 2,154,846 A | 4/1939 | Heymann et al. | |
| 2,161,349 A | 6/1939 | Hadden | |
| 2,186,005 A | 1/1940 | Casto | |
| D122,815 S | 10/1940 | Crosby | |
| 2,218,072 A | 10/1940 | Runnels | |
| 2,225,331 A | 12/1940 | Campbell | |
| 2,233,936 A | 3/1941 | Campbell | |
| 2,253,210 A | 8/1941 | Psiharis | |
| 2,253,910 A | 8/1941 | Luenz | |
| 2,263,802 A | 11/1941 | Grusin | |
| 2,305,461 A | 12/1942 | Spyra | |
| 2,364,205 A | 12/1944 | Fuller | |
| 2,405,029 A | 7/1946 | Gallanty et al. | |
| 2,418,485 A | 4/1947 | Shipley | |
| 2,476,201 A | 7/1949 | Eugenia | |
| 2,491,274 A | 12/1949 | McNeill | |
| 2,512,059 A | 6/1950 | Haeusser | |
| 2,517,912 A | 8/1950 | Nathan | |
| 2,543,999 A | 3/1951 | Voss | |
| D162,941 S | 4/1951 | Ehrman | |
| 2,554,777 A | 5/1951 | Dangin | |
| 2,574,654 A | 11/1951 | Moore | |
| 2,583,750 A | 1/1952 | Runnels | |
| 2,642,604 A | 6/1953 | Ferrari | |
| 2,651,068 A | 11/1953 | Seko | |
| 2,686,325 A | 8/1954 | Silver | |
| 2,702,914 A | 3/1955 | Kittle et al. | |
| 2,708,762 A | 5/1955 | Kling et al. | |
| 3,103,680 A | 9/1963 | Krichmar | |
| 3,153,800 A | 10/1964 | Trotin | |
| 3,181,193 A | 5/1965 | Nobles et al. | |
| 3,195,537 A | 7/1965 | Blasi | |
| 3,230,562 A | 1/1966 | Birch | |
| 3,254,356 A | 6/1966 | Yao et al. | |
| 3,258,805 A | 7/1966 | Rossnan | |
| 3,337,893 A | 8/1967 | Fine et al. | |
| D213,669 S | 4/1969 | Miller | |
| 3,509,874 A | 5/1970 | Stillman | |
| 3,610,043 A | 10/1971 | Wemyss | |
| 3,633,237 A | 1/1972 | Bagube | |
| 4,168,704 A | 9/1979 | Wessel | |
| 4,299,208 A | 11/1981 | Blanc | |
| 4,328,604 A | 5/1982 | Adams | |
| 4,356,585 A | 11/1982 | Protell et al. | |
| 4,364,142 A | 12/1982 | Pangle | |
| D272,683 S | 2/1984 | Stocchi | |
| D272,687 S | 2/1984 | Stocchi | |
| D272,689 S | 2/1984 | Stocchi | |
| D272,690 S | 2/1984 | Stocchi | |
| D273,635 S | 5/1984 | Stocchi | |
| 4,455,704 A | 6/1984 | Williams | |
| 4,461,285 A | 7/1984 | Courtin | |
| 4,488,327 A | 12/1984 | Snider | |
| 4,571,768 A | 2/1986 | Kawashima | |
| 4,610,043 A | 9/1986 | Vezjak | |
| D287,072 S | 12/1986 | Pfleger | |
| 4,628,564 A | 12/1986 | Youssef | |
| D295,695 S | 5/1988 | Golzari | |
| 4,827,551 A | 5/1989 | Maser et al. | |
| 4,888,844 A | 12/1989 | Maggs | |
| D309,528 S | 7/1990 | Valenti | |
| 5,005,246 A | 4/1991 | Yen-Hui | |
| 5,027,796 A | 7/1991 | Linzey | |
| 5,032,082 A | 7/1991 | Herrera | |
| 5,040,260 A | 8/1991 | Michaels | |
| 5,120,225 A | 6/1992 | Amit | |
| 5,165,761 A | 11/1992 | Dirksing | |
| 5,176,427 A | 1/1993 | Weihrauch | |
| 5,226,197 A | 7/1993 | Nack et al. | |
| 5,230,118 A | 7/1993 | Chamma | |
| 5,242,235 A | 9/1993 | Li | |
| 5,249,327 A | 10/1993 | Hing | |
| 5,273,425 A | 12/1993 | Hoagland | |
| 5,305,489 A | 4/1994 | Lage | |
| D350,851 S | 9/1994 | Spence, Jr. | |
| 5,392,483 A | 2/1995 | Heinzelman et al. | |
| 5,396,678 A | 3/1995 | Bredall et al. | |
| 5,438,726 A | 8/1995 | Leite | |
| 5,445,825 A | 8/1995 | Copelan et al. | |
| 5,511,273 A | 4/1996 | Carroll | |
| 5,530,981 A | 7/1996 | Chen | |
| 5,535,474 A | 7/1996 | Salazar | |
| 5,570,487 A | 11/1996 | Schneider | |
| D376,695 S | 12/1996 | Tveras | |
| 5,584,690 A | 12/1996 | Maassarani | |
| 5,604,951 A | 2/1997 | Shipp | |
| 5,613,262 A | 3/1997 | Choy-Maldonado | |
| 5,628,082 A | 5/1997 | Moskovich | |
| D386,905 S | 12/1997 | Brady et al. | |
| 5,709,004 A | 1/1998 | Paduano et al. | |
| D390,706 S | 2/1998 | Hohlbein et al. | |
| D391,769 S | 3/1998 | Kling et al. | |
| 5,735,011 A | 4/1998 | Asher | |
| 5,735,864 A * | 4/1998 | Heisinger, Jr. | 606/161 |
| 5,758,380 A | 6/1998 | Vrignaud | |
| 5,765,252 A | 6/1998 | Carr | |
| 5,766,193 A | 6/1998 | Millner | |
| D396,288 S | 7/1998 | Samuel | |
| 5,778,475 A | 7/1998 | Garcia | |
| 5,778,476 A | 7/1998 | Squillaci et al. | |
| 5,779,654 A | 7/1998 | Foley et al. | |
| D397,219 S | 8/1998 | Rangel et al. | |
| 5,792,159 A | 8/1998 | Amin | |
| 5,802,656 A | 9/1998 | Dawson et al. | |
| 5,810,856 A | 9/1998 | Tveras | |
| D399,349 S | 10/1998 | Barth | |
| 5,817,114 A | 10/1998 | Anderson et al. | |
| 5,818,856 A | 10/1998 | Injeyan et al. | |
| D401,069 S | 11/1998 | Lamond et al. | |
| D402,116 S | 12/1998 | Magloff et al. | |
| 5,845,358 A | 12/1998 | Woloch | |
| D403,510 S | 1/1999 | Menke et al. | |
| D404,205 S | 1/1999 | Hohlbein | |
| D404,206 S | 1/1999 | Hohlbein | |
| D405,272 S | 2/1999 | Khalaj et al. | |
| D407,221 S | 3/1999 | Van Gelder | |
| D407,222 S | 3/1999 | Van Gelder | |

| | | |
|---|---|---|
| D407,223 S | 3/1999 | Van Gelder |
| 5,875,510 A | 3/1999 | Lamond et al. |
| 5,896,614 A | 4/1999 | Flewitt |
| 5,913,346 A | 6/1999 | Narwani |
| 5,915,433 A | 6/1999 | Hybler |
| 5,920,941 A | 7/1999 | Iannotta |
| 5,928,254 A | 7/1999 | Jensen |
| 5,930,860 A | 8/1999 | Shipp |
| 5,938,673 A | 8/1999 | DePierro et al. |
| 5,946,759 A | 9/1999 | Cann |
| 5,951,578 A | 9/1999 | Jensen |
| 5,957,942 A | 9/1999 | Yudelman |
| 5,967,152 A | 10/1999 | Rimkus |
| 5,970,564 A | 10/1999 | Inns et al. |
| 5,980,541 A | 11/1999 | Tenzer |
| 5,980,542 A | 11/1999 | Saldivar |
| 5,984,935 A | 11/1999 | Welt et al. |
| 6,004,334 A | 12/1999 | Mythen |
| 6,015,293 A | 1/2000 | Rimkus |
| D420,515 S | 2/2000 | Van Gelder |
| D421,844 S | 3/2000 | Stark et al. |
| 6,032,315 A | 3/2000 | Liebel |
| 6,041,467 A | 3/2000 | Roberts et al. |
| D422,413 S | 4/2000 | Goldinger et al. |
| D423,785 S | 5/2000 | Karallis |
| D423,786 S | 5/2000 | Zelinski |
| D423,787 S | 5/2000 | Musciano |
| D424,808 S | 5/2000 | Beals et al. |
| D424,809 S | 5/2000 | Bernard |
| D425,306 S | 5/2000 | Beals et al. |
| 6,058,541 A | 5/2000 | Masterman et al. |
| D428,702 S | 8/2000 | Van Gelder |
| 6,098,233 A | 8/2000 | Chen |
| 6,105,191 A | 8/2000 | Chen et al. |
| 6,108,851 A | 8/2000 | Bredall et al. |
| 6,108,869 A | 8/2000 | Meessmann et al. |
| 6,119,296 A | 9/2000 | Noe et al. |
| 6,131,228 A | 10/2000 | Chen et al. |
| D434,906 S | 12/2000 | Beals et al. |
| 6,171,323 B1 | 1/2001 | Potti et al. |
| D440,767 S | 4/2001 | Moskovich et al. |
| 6,254,390 B1 | 7/2001 | Wagner |
| 6,260,227 B1 | 7/2001 | Fulop et al. |
| 6,276,021 B1 | 8/2001 | Hohlbein |
| 6,289,545 B1 | 9/2001 | Molster |
| D448,569 S | 10/2001 | Harris et al. |
| 6,308,367 B1 | 10/2001 | Beals et al. |
| 6,322,573 B1 | 11/2001 | Murayama |
| 6,345,405 B1 | 2/2002 | Brackin |
| 6,352,545 B1 | 3/2002 | Wagner |
| 6,353,958 B2 | 3/2002 | Weihrauch |
| D456,139 S | 4/2002 | Hohlbein |
| 6,374,448 B2 | 4/2002 | Seifert |
| D456,607 S | 5/2002 | Carlucci et al. |
| 6,383,202 B1 | 5/2002 | Rosenblood et al. |
| D459,087 S | 6/2002 | Pfleger |
| 6,402,768 B1 | 6/2002 | Liebel |
| 6,408,476 B1 | 6/2002 | Cann |
| 6,421,867 B1 | 7/2002 | Weihrauch |
| D461,959 S | 8/2002 | Chan et al. |
| 6,440,149 B1 | 8/2002 | Potti |
| D463,131 S | 9/2002 | Winter et al. |
| 6,446,295 B1 | 9/2002 | Calabrese |
| D464,796 S | 10/2002 | Winter et al. |
| 6,463,619 B2 | 10/2002 | Gavney, Jr. |
| D465,847 S | 11/2002 | Jacobs |
| 6,496,999 B1 | 12/2002 | Gleason et al. |
| 6,513,182 B1 | 2/2003 | Calabrese et al. |
| D471,276 S | 3/2003 | Potti |
| 6,546,586 B2 | 4/2003 | Cho |
| 6,571,417 B1 | 6/2003 | Gavney, Jr. |
| D477,465 S | 7/2003 | Reilly et al. |
| D478,211 S | 8/2003 | Ping |
| 6,625,839 B2 | 9/2003 | Fischer |
| D482,199 S | 11/2003 | DeSalvo |
| 6,647,581 B1 | 11/2003 | Persad et al. |
| D483,184 S | 12/2003 | Geiberger et al. |
| D483,568 S | 12/2003 | Jamson |
| D486,649 S | 2/2004 | Sprosta et al. |
| 6,729,789 B2 | 5/2004 | Gordon |
| 6,792,642 B2 | 9/2004 | Wagstaff |
| 6,817,054 B2 | 11/2004 | Moskovich et al. |
| 6,820,299 B2 | 11/2004 | Gavney, Jr. |
| 6,859,969 B2 | 3/2005 | Gavney et al. |
| 6,865,767 B1 | 3/2005 | Gavney, Jr. |
| D503,538 S | 4/2005 | DeSalvo |
| 6,886,207 B1 | 5/2005 | Solanki |
| 6,895,629 B1 | 5/2005 | Wenzler |
| 2001/0023516 A1 | 9/2001 | Driesen et al. |
| 2001/0041903 A1 | 11/2001 | Richard |
| 2001/0042280 A1 | 11/2001 | Moskovich et al. |
| 2002/0004964 A1 | 1/2002 | Luchino et al. |
| 2002/0019645 A1 | 2/2002 | Fischer et al. |
| 2002/0108194 A1 | 8/2002 | Carlucci et al. |
| 2002/0124333 A1 | 9/2002 | Hafliger et al. |
| 2002/0124337 A1 | 9/2002 | Calabrese et al. |
| 2002/0138926 A1 | 10/2002 | Brown, Jr. et al. |
| 2002/0138928 A1 | 10/2002 | Calabrese et al. |
| 2002/0147418 A1 | 10/2002 | Huang |
| 2003/0009837 A1 | 1/2003 | Cann |
| 2003/0115699 A1 | 6/2003 | Wagstaff |
| 2003/0163149 A1 | 8/2003 | Heisinger, Jr. |
| 2003/0167582 A1 | 9/2003 | Fischer et al. |
| 2003/0196283 A1 | 10/2003 | Gatzemeyer et al. |
| 2003/0208865 A1 | 11/2003 | Davies |
| 2003/0216762 A1 | 11/2003 | Levit |
| 2003/0229959 A1 | 12/2003 | Gavney, Jr. et al. |
| 2004/0006837 A1 | 1/2004 | Cann |
| 2004/0025275 A1 | 2/2004 | Moskovich et al. |
| 2004/0031115 A1 | 2/2004 | Gavney, Jr. |
| 2004/0068810 A1 | 4/2004 | Lee |
| 2004/0134007 A1 | 7/2004 | Davies |
| 2004/0221409 A1 | 11/2004 | Gavney, Jr. |
| 2004/0231076 A1 | 11/2004 | Gavney, Jr. |
| 2004/0237236 A1 | 12/2004 | Gavney, Jr. |
| 2004/0255416 A1 | 12/2004 | Hohlbein |
| 2005/0000049 A1 | 1/2005 | Hohlbein |
| 2005/0015904 A1 | 1/2005 | Gavney, Jr. |
| 2005/0038461 A1 | 2/2005 | Phillips |
| 2005/0069372 A1 | 3/2005 | Hohlbein et al. |
| 2005/0210612 A1 | 9/2005 | Hohlbein et al. |

FOREIGN PATENT DOCUMENTS

| | | |
|---|---|---|
| DE | 2930459 | 2/1981 |
| DE | 3114507 | 3/1983 |
| DE | 3639424 | 6/1988 |
| DE | 101 22 987 | 10/2002 |
| DE | 201 07 614 | 10/2002 |
| DE | 20 2005 009 026 | 11/2005 |
| EP | 0875169 | 4/1998 |
| EP | 1 034 721 | 9/2000 |
| EP | 1308108 | 5/2003 |
| FR | 537979 | 6/1922 |
| FR | 2594307 | 4/1987 |
| GB | 17643 | 0/1912 |
| GB | 495982 | 11/1938 |
| GB | 2371217 | 7/2002 |
| GB | 2391462 | 2/2004 |
| JP | 2000-278899 | 10/2000 |
| JP | 2000-308522 | 11/2000 |
| JP | 2001-161720 | * 6/2001 |
| JP | 2001-314232 | 11/2001 |
| JP | 2001314232 | 11/2001 |
| JP | 2002-142867 | 5/2002 |
| NZ | 99225704.2 | 11/1999 |
| SE | 99738 | 6/1923 |
| SU | 1708283 | 12/1989 |
| WO | WO 96/15696 | 5/1996 |
| WO | WO 98/05241 | 2/1998 |
| WO | 9808458 | 3/1998 |
| WO | WO 98/09573 | 3/1998 |
| WO | 9822000 | 5/1998 |
| WO | WO 99/33374 | 7/1999 |
| WO | WO 99/49754 | 10/1999 |

| | | | | | |
|---|---|---|---|---|---|
| WO | WO 00/64307 | 2/2000 | WO | WO 02/071967 | 9/2002 |
| WO | WO 01/17433 | 3/2001 | WO | WO 03/030680 | 4/2003 |
| WO | WO 01/45573 | 6/2001 | WO | WO 2004/019801 | 3/2004 |
| WO | 01/80686 | * 11/2001 | | | |
| WO | WO 01/80686 | 11/2001 | | | |

* cited by examiner

ORAL CARE IMPLEMENT

CROSS-REFERENCE TO RELATED APPLICATIONS

The present application is a divisional of U.S. application Ser. No. 11/261,048, filed Oct. 28, 2005, U.S. Pat. No. 7,594,293, which is a continuation-in-part of U.S. application Ser. No. 11/011,605 filed Dec. 15, 2004, U.S. Pat. No. 7,725,980, both of which are incorporated herein by reference in their entirety.

This application is also a continuation-in-part of U.S. application Ser. No. 11/019,671, filed Dec. 23, 2004, U.S. Pat. No. 7,721,376, which is (1) a continuation-in-part of U.S. application Ser. No. 10/869,922, filed Jun. 18, 2004, U.S. Pat. No. 7,143,462, which is a continuation in part of U.S. application Ser. No. 10/601,106, filed Jun. 20, 2003, abandoned (2) a continuation in part of International Application PCT/US2003/030633 filed Sep. 26, 2003, which claims the benefit of U.S. Application 60/414,117, filed Sep. 27, 2002, U.S. Application 60/418,776, filed Oct. 16, 2002, and U.S. Application 60/419,425, filed Oct. 18, 2002, (3) a continuation in part of International Application PCT/US2003/029497, filed Sep. 17, 2003, which claims the benefit of U.S. Application 60/412,290, filed Sep. 20, 2002, (4) a continuation-in-part of U.S. application Ser. No. 29/189,729, filed Sep. 10, 2003, U.S. Pat. No. Des. 517,812, and (5) a continuation-in-part of U.S. application Ser. No. 10/989,267, filed Nov. 17, 2004, U.S. Pat. No. 7,607,189, which is a continuation-in-part of U.S. application Ser. No. 29/209,242, filed Jul. 14, 2004, abandoned. The contents of the above-noted applications are each expressly incorporated herein by reference.

FIELD OF THE INVENTION

The present invention pertains to an oral care implement with a tongue cleanser for cleansing the tongue and other soft tissue in the mouth.

BACKGROUND OF THE INVENTION

According to the American Dental Association, bad breath in healthy people is often attributable to microbial deposits on the tongue. Due to its papillary nature, the tongue creates a unique ecological site that provides a large surface area, which favors the accumulation of oral bacteria. Anaerobic flora and bacteria residing on the tongue can lead to the development of chronic bad breath commonly called halitosis.

While tongue scrapers have been used in the past, these scrapers have not adequately met the need. Past scrapers have typically been uncomfortable, risked injury to the user, and/or lacked effectiveness. Hence, there is a need for an oral care implement with a tongue cleanser that provides effective removal of bacteria and other debris with comfort and safety.

SUMMARY OF THE INVENTION

The present invention pertains to an oral care implement with a tongue cleanser provided with a unique combination of hard and soft materials to effectively cleanse the tongue and other soft tissue within the mouth with comfort and a reduced risk of injury to the user.

In one aspect of the invention, a tongue cleanser is formed of two components that combine to define at least one cleaning projection that extends from a head of an implement. One component of the tongue cleanser is composed of a relatively hard material to provide stability and effective cleaning of the soft tissue. The other component is composed of a relatively soft material to provide comfort and safety to the user during use of the implement.

In one exemplary construction of the invention, the tongue cleanser includes a base composed of a relatively hard material that protrudes from a surface of the head, and a soft material that at least partially overlies the base. The hard base provides good stability for cleaning bacteria and debris from the tongue or other tissue, while the soft layer provides comfort and a reduced risk of injury. In one embodiment, the tip of the base is covered with the soft material. In another embodiment, a small extension of the base tip is exposed through the soft material.

In another exemplary construction, the tongue cleanser includes a projection formed of a soft material, which is embedded in a hard base for enhanced rigidity. In one embodiment, the projection is a tapering member with a narrow tip to engage and clean soft tissue in the mouth and a wide base portion anchored in a hard material portion of the head. The soft material engages the tongue for comfort and safety. The hard material provides enhanced stiffness and stability to the cleanser.

In another aspect of the invention, a tongue cleanser is formed of two components of various topographies. One component of the tongue cleanser is composed of a relatively hard material, while the other component is composed of a relatively soft material.

DETAILED DESCRIPTION OF THE INVENTION

Figure 1:
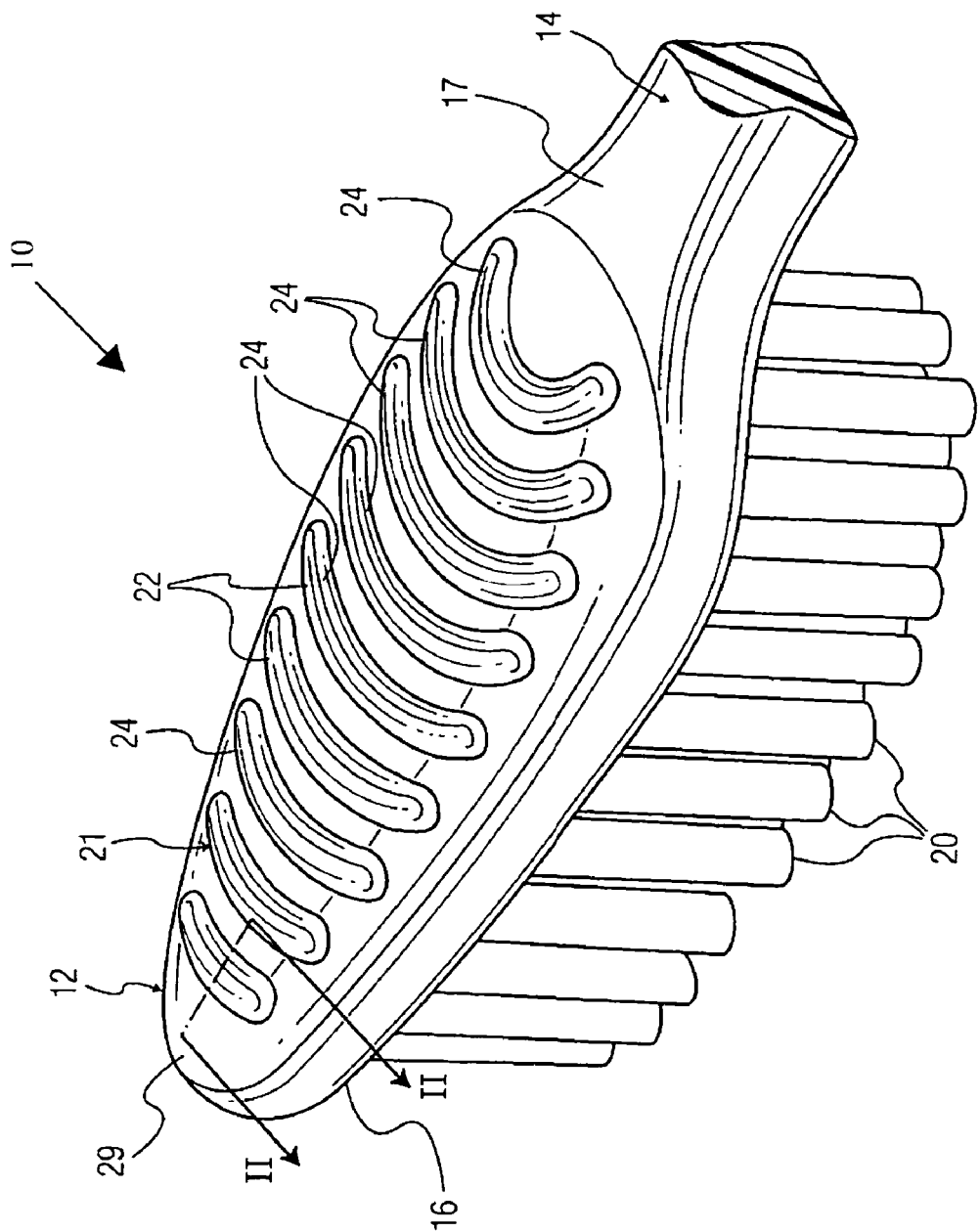
FIG. 1 is a perspective view of a head of a toothbrush in accordance with the present invention.
Figure 2:
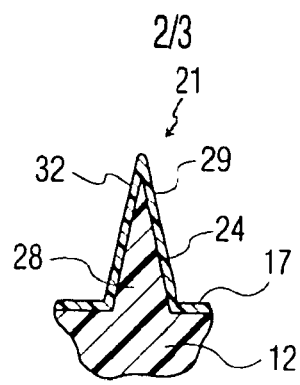
FIG. 2 is a partial cross-sectional view taken along line II-II in FIG. 1.

An oral care implement in accordance with the present invention is illustrated and described in the form of a toothbrush 10 (FIGS. 1 and 2). Nevertheless, the invention could be encompassed into other oral care implements, including simply a tissue-cleansing implement. Toothbrush 10 includes a head 12 and a handle 14. While FIG. 1 only illustrates the connection of the handle to the head, the handle is preferably an elongate member to be grasped by the user. The handle 14 could have any known shape and construction adapted for the manipulation needed to clean the teeth and/or tongue of a user. Head 12 includes a pair of opposite sides 16, 17 with teeth cleaning elements 20 extending from side 16 and a soft tissue cleanser 21 provided on side 17. While such soft tissue cleanser 21 may be used to impact areas of the mouth other than the teeth, it is primarily intended for use as a tongue cleanser and will be described herein as such for purposes of convenience. Although head 12 is shown with an oblong shape, other known shapes could be used.

The teeth cleaning elements 20 could be bristles and/or elastomeric members of various shapes and sizes. Any form or combination of elements 20 suitable for cleaning a user's teeth could be used.

Tongue cleanser 21 includes at least one projection 22, and preferably a plurality of projections, to cleanse the tongue and other soft tissue of the mouth (e.g., the inner surfaces of the cheeks). While the projections are preferably formed on a head also provided with teeth cleaning elements 20, they could be formed on other implements or other parts of the toothbrush. Any reference to a head of an implement is simply meant to be a reference to the operative portion of the implement that is inserted into the mouth, and does not refer to a particular shape, structure or location of the head. In the present invention, each of the projections is formed by a combination of hard and soft materials to provide the beneficial effects of superior cleaning of the tongue (or other soft tissue) with comfort and safety from injury.

In one embodiment (FIGS. 1 and 2), a plurality of projections 22 are formed to extend across a back side 17 of head 12. Each projection includes a base portion 28 protruding from the head, and a layer 29 overlying the base portion (FIG. 2). Base 28 is composed of a relatively rigid material such as Polypropylene, although many other materials could be used. The base portion is preferably formed as part of the head as shown in FIG. 2, but could be separately formed and attached to the head by adhesive, fasteners or the like. Layer 29 is preferably a thermoplastic elastomer such as Santoprene, Thermolast-K, Dynaflex, although many other materials could also be used so long as they are compatible for oral care and soft enough to provide the desired comfort and/or safety benefits. While projections 22 are described and shown as ridges 24, they could have a non-ridge construction (e.g., columnar or conical) if desired. Various shapes and cross-sectional configurations of projections 22 are contemplated.

Figure 3:
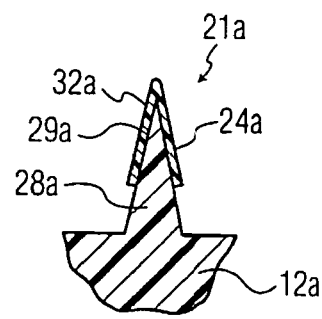
FIGS. 3-6 are partial cross sectional views alternative structures taken along line II-II of FIG. 1.

In this one construction, base 28 tapers to a narrow tip 32 to better dig into the recesses in the tongue and remove bacteria and debris. As shown, the base can be formed to have a generally triangular cross section, though other narrowing shapes could be used. Moreover, constant cross-sectional shapes, non-tapering shapes or those that do not taper to a narrow tip could also be used if desired. The soft overlayer 29 overlies the entire back side 17 of head 12 for enhanced comfort and safety; i.e., layer 29 protects users from cutting or injuring their tongues or other tissue even when very narrow tips are used to define ridges 24. Soft layer 29 is preferably molded over side 17 of head 12, but could be otherwise secured such as by adhesive, fasteners, etc. Alternatively, a soft layer or covering 29a could be formed to cover only the tips 32a of ridges 24a of tongue cleanser 21a (FIG. 3). Of course, other variations in coverage of the projections by overlayer 29 could be used. For example, the soft material component 29 could cover more or less of the base 28 than is shown in FIG. 3, or could cover bases 28 and only a part of side 17 of head 12 without covering the entire side. In one example, base 28 extends 0.5 to 1 mm from side 17 of head 12, and soft material component 29 is 0.3 to 0.5 mm thick. Nevertheless, many other smaller and greater extensions and thicknesses could be used to form projections.

Figure 4:
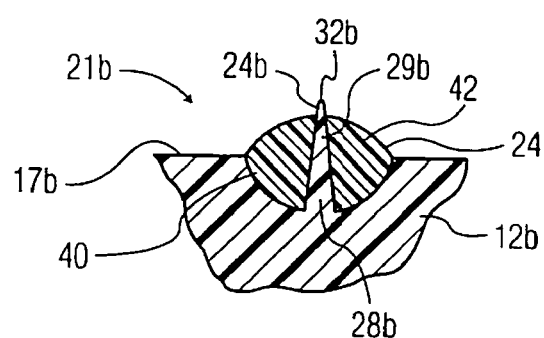

In one other embodiment (FIG. 4), tongue cleanser 21b includes at least one ridge 24b defined by a base portion 28b and an overlayer 29b. As with the earlier embodiment, base 28b is formed of a relatively hard material, which in the preferred construction is formed as a unitary portion of the head. As with the earlier embodiment, base 28b preferably tapers to a narrow tip 32b to effectively remove bacteria and debris, although other shapes could be used. Overlayer 29b is composed of a relatively soft material, which partially covers base portion 28b. However, in this construction, the tip 32b of base portion 28b is left uncovered, while the remaining portion of the base is covered by the soft component 29b. Nevertheless, comfort and safety are maintained with the exposed tip 32b, even when narrowed, by limiting the extension of the exposed tip beyond the soft material 29b. More specifically, tongues or other soft tissue within the mouth tend to give or flex as the ridges contact and move over them. This flexibility enables a short tip 32b to pass over the tongue or other tissue without injuring the user. As a result, comfort and safety are maintained.

In one such construction, base portion 28b protrudes outward from a recess 40 formed in side 17b of head 12b. In this example, since base 28b is formed as an elongate ridge, recess 40 has the form of an elongate channel extending across side 17b. If the projection were instead, for example, columnar, the recess would then preferably encircle the projection. The soft component 29b fills and is secured in recess 40 about base 28, and defines an outer surface 42 that gradually extends to a position proximate tip 32b. In the illustrated example, outer surface 42 of overlayer 29 has a broad curved, convex shape against which the tongue or other tissue slides. This outer surface, however, could have many different shapes so long as it provides a surface against which the tongue or other tissue can slide and be exposed to only a small portion of the underlying base 28b. In this one example shown in FIG. 4, base 28b has a height (i.e., from the bottom of recess 40 to tip 32b) of 1 mm, and extends 0.5 mm beyond outer surface 42, though these dimensions could vary considerably. Moreover, the construction could vary. For example, recess 40 could be eliminated and the hard component formed as a shorter base that extends directly from a generally planar back side 17. In this construction, soft component would preferably be a generally uniform layer overlying at least part of the back side of the head and part of the base. Also, alternatively, the tip portion of the relatively hard first component could be secured to the relatively soft second component (not shown) rather than the being directly fixed to the head.

In another embodiment (FIG. 5), tongue cleanser 21c is formed by a soft material component 29c that defines a projection 48 which is embedded in a relatively hard base 49, preferably a hard base portion of head 12c. In this construction, projection 48 preferably protrudes from a recess 50 defined in side 17c of head 12c; although recess 50 could be omitted. Projection 48 preferably extends outwardly from the recess 50 and above a plane 55 defined by the side 17c such that the projection 48 is raised relative to the side 17c to provide increased cleaning benefits. Nevertheless, tip 56 of the projection may be generally co-extensive with plane 55 so long as contact with the soft tissue still occurs. Recess 50 is similar to recess 40 discussed above, except that in this construction the recess remains open. In this example, since the projection is formed as an elongate ridge, recess 50 would be an elongate channel extending across the head. Ridge 48 is anchored into the head to provide a stiffer member, despite being a soft material, to provide an effective cleansing of the tongue and other tissue. In the illustrated example, ridge 48 has a height (extending from the bottom of recess 50) of about 1 mm, and a projection above back side 17c of about 0.5 mm. Nevertheless, wide variations from these dimensions may be used.

In the one construction, projection 48 includes an anchoring portion 54 that is embedded in base 49 (which is preferably a portion of head 12) and a tip 56 for contacting the soft tissue. Projection 48 preferably tapers from anchoring portion 54 to tip 56 to define a narrowed tip for effectively cleaning of the tongue and other tissue, and a broad anchoring portion for greater support and stiffness. Nevertheless, other tapering and non-tapering projections could be used.

Figure 5:
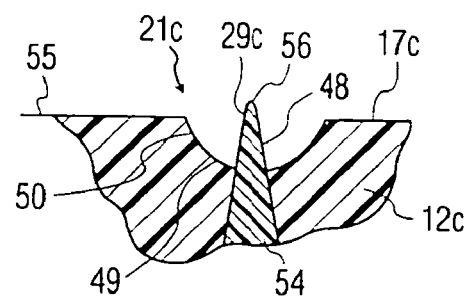
Figure 6:
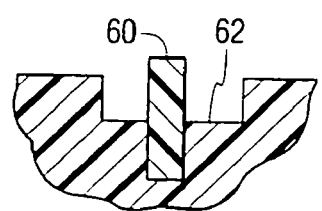

Furthermore, the construction of FIG. 5 illustrates one example of a concavity defined within side 17c (i.e., the recess 50) that includes a tissue-cleaning convexity (i.e., projection 48) extending outwardly therefrom. As noted above, the concavity can be defined as an elongate depression or ridge or a hemispherical recess, with other concavities being contemplated. In addition, the convexity can be any shape and/or cross-section including, but not limited to, those projection shapes disclosed herein. For instance, the convexity can be a column 60 of constant cross-section extending from a concavity 62 of square profile as shown in FIG. 6.

Figure 7:
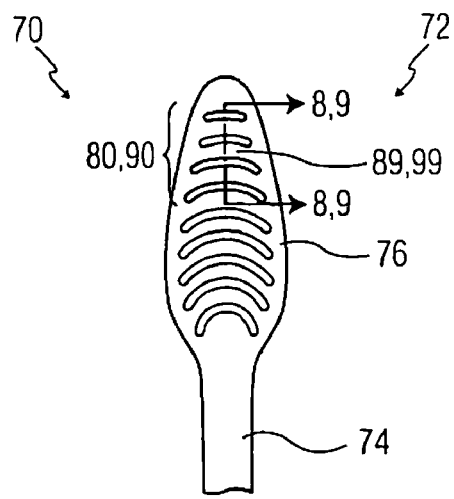
FIG. 7 is a front view of the rear of a head of a toothbrush in accordance with another embodiment of the present invention.

In another construction (FIGS. 7-9), an oral care implement such as a toothbrush 70 includes a head 72, a handle 74 and a plurality of soft tissue-cleaning projections 80 disposed along a back side 76 of the head 72. Tooth-cleaning elements (not shown in FIGS. 7-9) are formed on the opposite side of the head as shown in FIG. 1. While FIG. 7 shows a plurality of arcuate projections of varying curvature, it will be understood that other constructions and configurations may be used as desired.

Figure 8:
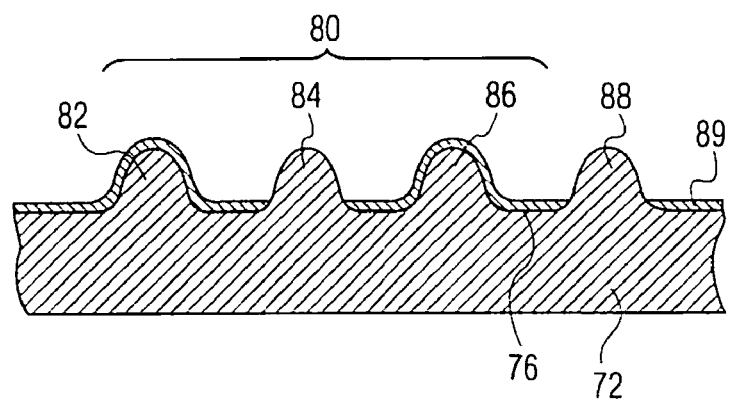
FIG. 8 is a cross-sectional view of one embodiment taken along line 8-8 of FIG. 7.

In the embodiment of FIG. 8, projections 82, 84, 86 and 88 are formed integral with the head 72 and from the same material as the head 72. The head material is preferably each formed of a relatively rigid material such as polypropylene, although other materials could be used. Of course, while such projections are shown as formed as part of the head, such projections could also be separately formed and attached to the head by adhesive, fasteners or the like. Overlying projections 82 and 86, as well as a majority of the back side 76, is a layer 89 that is preferably formed from a material that is softer than the head material. Such layer 89 leaves projections 84 and 88 exposed on the back side 76. Layer 89 is preferably molded over side 76 of head 72, but could be otherwise secured such as by adhesive, fasteners, etc., and is preferably formed from a thermoplastic elastomer such as Santoprene, Thermolast-K, Dynaflex, although many other materials could also be used so long as they are compatible for oral care and soft enough to provide the previously-discussed desired comfort and/or safety benefits. While projections 80 are described and shown as ridges, they could have a non-ridge construction (e.g., columnar or conical) if desired, with various shapes and cross-sectional configurations being contemplated.

The embodiment of FIG. 8 illustrates a multi-component soft tissue cleaner having projections of a first material and other projections of a second material. Thus, the user is able to sense and take advantage of the different functionalities inherent is a relatively hard projection component and a relatively soft projection component, to provide an effective cleansing of the tongue and other soft tissue in the mouth.

Figure 9:
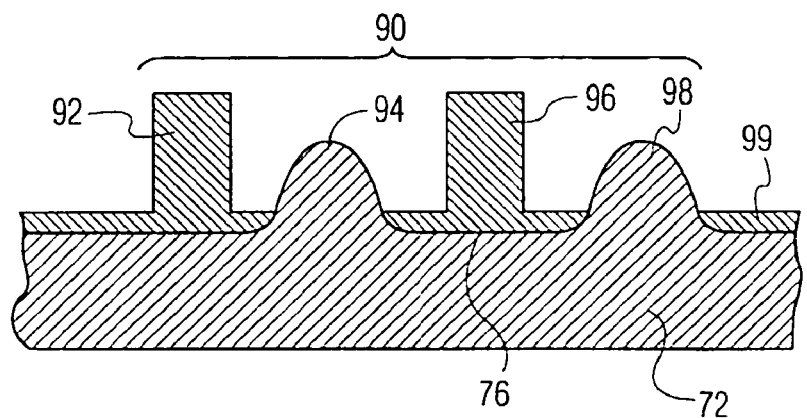
FIG. 9 is a cross-sectional view of another embodiment taken alone line 9-9 of FIG. 7.

In the embodiment of FIG. 9, projections 94 and 98 are formed from the same material as the head 72 and preferably also formed integral with the head 72, while projections 92 and 96 are formed from an overlayer 99 of a material that is different from the head material. As with the embodiment of FIG. 8, the head material is preferably each formed of a relatively rigid material such as polypropylene, while the overlayer 99 is preferably formed from a material that is less rigid, such as a thermoplastic elastomer, and that is overmolded onto the head 72. While projections 90 have differing heights and cross-sections, it will be understood that a variety of configurations of different or similar structural characteristics may be used as desired.

Although the tongue or soft tissue cleanser of the present invention has been discussed primarily in connection with a plurality of ridges that extend laterally across the head, the concepts of the invention are applicable to all kinds of projections usable as a tongue or soft tissue cleanser. For example, the ridges may have all kinds of shapes, sizes, heights and configurations on the head as disclosed, for example, in U.S. application Ser. No. 10/989,267, filed Nov. 17, 2004, which is hereby incorporated by reference. Moreover, the projections may be formed as non-ridge projections or a mixture of ridge and non-ridge projections, such as disclosed, for example, in U.S. application Ser. No. 10/989,267 or in U.S. application Ser. No. 10/869,922.

Also various other changes could be made in the above disclosed constructions without departing from the scope of the invention, it is intended that all matter contained in this application, including all mechanisms and/or modes of interaction described above, shall be interpreted as illustrative only and not limiting in any way the scope of the appended claims.

What is claimed is:

1. An oral care implement comprising a head having a first projection and a second projection protruding from a first side and to cleanse soft tissue within a user's mouth, the first projection being formed of a first material and having a tip, a first portion of the second projection being formed by the first material and a second portion of the second projection being formed by a second material that is different from the first material, at least a portion of the first side being covered by the second material, the tip of the first projection being free of the second material.

2. The oral care implement of claim 1, wherein the first material is a relatively hard material and the second material is a relatively soft material.

3. The oral care implement of claim 2, wherein the first material is a hard plastic material and the second material is an elastomeric material.

4. The oral care implement of claim 3, wherein the second material is a thermoplastic elastomer.

5. The oral care implement of claim 1, wherein at least a portion of the head is formed from the first material.

6. The oral care implement of claim 5, wherein the first projection is integral with the head.

7. The oral care implement of claim 6, wherein the second material overlies substantially the entire first side of the head.

8. The oral care implement of claim 7, wherein teeth cleaning elements extend from a second side of the head, which is opposite the first side.

9. The oral care implement of claim 7, further comprising a plurality of first projections.

10. The oral care implement of claim 1, wherein the first portion of the second projection that is formed from the first material is covered by the second material.

* * * * *